US005601838A

United States Patent [19]

Hind

[11] Patent Number: 5,601,838
[45] Date of Patent: *Feb. 11, 1997

[54] METHOD FOR TREATING PAIN ASSOCIATED WITH HERPES-ZOSTER AND POST-HERPETIC NEURALGIA

[75] Inventor: Harry Hind, Los Altos, Calif.

[73] Assignee: Hind Health Care, Inc., Los Altos, Calif.

[*] Notice: The portion of the term of this patent subsequent to May 2, 2012, has been disclaimed.

[21] Appl. No.: 526,771

[22] Filed: May 18, 1990

Related U.S. Application Data

[63] Continuation of Ser. No. 325,373, Mar. 17, 1989, abandoned.

[51] Int. Cl.⁶ .............................. A61K 9/70; A61L 15/00
[52] U.S. Cl. ..................... 424/443; 424/401; 424/445; 424/447; 424/448; 424/449
[58] Field of Search ................................ 424/445, 448, 424/449

[56] References Cited

U.S. PATENT DOCUMENTS 5,411,738  5/1995  Hind .......................................... 424/445

FOREIGN PATENT DOCUMENTS

| 0276561 | 8/1988 | European Pat. Off. . |
| 0297828 | 1/1989 | European Pat. Off. . |
| 0331392 | 9/1989 | European Pat. Off. . |
| 62-51617 | 3/1987 | Japan . |
| 1108837 | 11/1966 | United Kingdom . |
| 88/09169 | 12/1988 | WIPO . |

OTHER PUBLICATIONS

Hanks and White *Br. Med. J.* (1988) 297:1215.
Milligan et al. *Br. Med. J.* (1989)298:188.
Rowbotham and Fields *Pain* (1989) 38:297–301.
Reiz et al., *Arta Anaesth. Scand.* (1982) 26:596–598.
McCafferty et al., *Br. J. Anaesth.* (1988) 60:64–69.
Lubens et al., *Am. J. Dis. Child.* (1974) 128:192–194.
Hallen et al., *Anesthesiology* (1982) 57:340–342.
William Curatolo in *Pharmaceutical Research* (1987) 4:271–277.
Dalvi et al., *J. Soc. Cosmet. Chem.* (1981) 32:87–94.
Shahi et al., *Journal of Pharmaceutical Sciences* (1978) 67:789–792.
Addicks et al., *Pharmaceutical Research* (1988) 5:377–382.
Ostrenga et al., *Journal of Pharmaceutical Sciences* (1971) 60:1175–1179.
Turi et al., *Journal of Pharmaceutical Sciences* (1979) 68:275–279.
Barry et al., *J. Pharm. Pharmacol.* (1985) 37:84–90.
Sarpotdar et al., *Journal of Pharmaceutical Sciences* (1986) 75:176–181.
Stow et al., *Annual Meeting of the Scandinavian Association for the Study of Pain in joint meeting with The Intractable Pain Society of Great Britain and Ireland* (1989).
Stow et al. *Pain* (1989) 38:297–301.
Robert B. King, *Pain* (1988) 33:73–78.
Russo et al., *Am. J. Hosp. Pharm.* (1980) 37:843–847.
Juhlin et al., *Acta Dermatovener* (Stockholm) (1980) 60:554–546.

*Primary Examiner*—Thurman K. Page
*Assistant Examiner*—Sharon Howard
*Attorney, Agent, or Firm*—Flehr, Hohbach, Test, Albritton & Herbert; Bertram I. Rowland

[57] ABSTRACT

A method is offered for reducing the pain associated with herpes-zoster and post-herpetic neuralgia. The method consists of administering a composition incorporating a transdermal delivery system for the administration of Lidocaine to areas of the body afflicted by herpes-zoster and post-herpetic neuralgia enclosed with an occlusive dressing or a plaster dressing.

6 Claims, No Drawings

METHOD FOR TREATING PAIN ASSOCIATED WITH HERPES-ZOSTER AND POST-HERPETIC NEURALGIA

This application is a continuation of U.S. application Ser. No. 07/325,373, filed Mar. 17, 1989, now abandoned.

TECHNICAL FIELD

The subject of this application concerns methods for treatment of pain associated with herpes-zoster and post-herpetic neuralgia.

BACKGROUND

The acute neuralgia produced by recrudescence of latent varicella-zoster virus (familiarly known as chicken pox virus) is called herpes-zoster, or "shingles". Reactivation of the latent virus in a dorsal root ganglion results in the transport of live virus along the associated sensory nerves (dermatome).

In addition to severe pain in the distribution of affected nerves, herpes zoster is also associated with nervous system complications such as myelitis, stroke, ocular damage, skin damage, and, most commonly, post-herpetic neuralgia—defined as pain that persists in the involved dermatome for more than 1 month after healing of the skin lesions.

Over 50% of people over age 60 who have acute herpetic neuralgia can expect to be afflicted with PHN. The disorder resolves spontaneously within 1 year in most cases, but in some the pain persists for life.

Pain management in both herpes zoster and post-herpetic neuralgia is unsatisfactory. Non-steroidal anti-inflammatory medications and opiates are often of little benefit. The only drug with proven effectiveness in a controlled study is the tricyclic antidepressant amitripyline. This drug has multiple effects that are not well tolerated by elderly patients, and pain relief is incomplete.

Other medications—anticonvulsants (eg, carbamazepine) and neuroleptics (eg, chlorprothixene)—are widely used but have not proved to be effective. Several topical preparations, including salicylate poultices, ethyl chloride spray, idoxurine (an anti-viral agent) in DMSO, and others have been anecdotally reported to be effective.

Local anesthetics, such as lidocaine, have been administered parenterally to relieve the pain of herpes zoster and post-herpetic neuralgia: as regional sympathetic blocks, as peripheral nerve blocks, by epidural infusion, by direct subcutaneous infiltration, and intravenously.

However, topical application of local anesthetics is not a presently recognized method of treating pain associated with herpes zoster and post-herpetic neuralgia.

RELEVANT LITERATURE

The following are representative of the medical literature pertaining to management of post-herpetic neuralgia and herpes zoster:

King R B, in *Pain* 1988;33:73–78, describes the use of an aspirin/chloroform mixture to treat post-herpetic neuralgia and herpes zoster Dan K et al, in *Advances in Pain Research and Therapy* vol 9, Field et al (editors), Raven Press, New York (1985), pages 831–838, describe the use of nerve block to treat herpetic pain Watson C P et al, in *Neurology* 1982;32:671–673, describe the use of amitriptyline for treatment of post-herpetic neuralgia.

Colding A, in *Proc R Soc Med* 1971;66:541–543, describes the use of local anesthetics to treat herpetic pain.

Secunda L et al, in *N Engl J Med* 1941;224:501–503, describe the treatment of herpetic pain through cutaneous infiltration of local anesthetics.

Hallen B et al, in *Anesthesiology* 1982;57:340–342, describe the use of lidocaine-prilocaine cream to reduce the pain associated with bladder catheter insertion.

Luben H M et al, in *Am J Dis Child* 1974;128:92–194, describe the use of a 30% lidocaine patch for anesthesia in minor surgery.

Russo J et al, in *Am J Hosp Pharm* 1980;37:843–847, compare the effectiveness of different methods of lidocaine administration.

Sarpotdar P and Zatz J in *J Pharm Sciences* 1986;75:176–181 (title) Evaluation of Penetration Enhancement of Lidocaine by Nonionic Surpitants through Hairless Mouse Skin In Vitro.

Reiz G M E E and Reiz S L A in *Acta Anaesth Scand* 1982;26:596–598 describe a topical anaesthetic compound.

Mollgaard B and Hoelgaard A, in *Acta Pharm Suec* 1983;20:43–450 describe drug permeation formulations.

Vaughn C, in *Cosmetics and Toiletries* 1988;103:47–68, describes cohesive energies of compounds for determining solubility and miscibility.

SUMMARY OF THE INVENTION

A method for reducing the pain of herpes-zoster and post-herpetic neuralgia is provided. It involves topical application of a compound consisting of a local anesthetic and a vehicle for transdermal delivery of medication under a dressing, usually an occlusive dressing or in a plaster dressing. The dressing enhance the effectiveness of the local anesthetic as evidenced by increases in duration of pain relief.

DESCRIPTION OF THE SPECIFIC EMBODIMENTS

A method for reducing pain associated with herpes-zoster and post-herpetic neuralgia is provided. It consists of applying to the skin at the site of involvement a composition consisting of a lidocaine and a vehicle for transdermal delivery of the medication under a dressing usually occlusive or plaster. This method provides pain relief for significantly longer periods of time than currently used methods and avoids the harmful effects associated with other less effective or completely ineffecive methods of treatment.

Lidocaine has the property of abolishing pain sensation at the site of application or injection. The compound is used for the management of pain due to herpes zoster and post-herpetic neuralgia.

The local anesthetic present in the gel and plaster formulations is in base form. The base in sufficient amounts will penetrate the skin to relieve the pain of herpes zoster and post herpetic-neuralgia.

Depending on the mode of administration, anesthetic concentrations will generally be in the range of about 5–50%. For gels, the concentration will vary from about 5% to 20%—usually 5–10%; for plasters, the concentration may range from 1% up to 20%.

The compound used for the treatment of pain associated with post-herpetic neuralgia and herpes zoster contains a vehicle for the purpose of increasing the effectiveness of transdermal delivery. The formulations vary depending on the manner of administration.

When a gel is used as a vehicle for enhancing transdermal delivery, the compounds employed (usually anhydrous compounds) include solvents such as polyols, particularly glycols (propylene glycol, hexylene glycol, dipropylene glycol, polyethylene glycol, tripropylene glycol, triethylene glycol, butylene glycol, and hexanetriol)—individually or in combination. These compounds are present in concentrations sufficient to promote transdermal delivery of the local anesthetic, usually present in concentrations of 70–90%—most commonly 75–85%.

The gel is used to facilitate application to the skin. Illustrative gelling agents are hydroxypropylcellulose acetate, polyethylene glycols, carbomer 940 (diisopropylpropanolamine-neutralized polyacrylate), etc. The gelling agent used will be in concentrations of about 0.1–5%.

Nonionic surfactants will also usually be employed—polysorbate esters and ethers, sorbitol esters and ethers, etc.—in concentration ranging from 2% to 20% also serving as cosolvents and skin penetration inhancers.

The vehicle may also contain other physiologically acceptable excipients such as fragrances, dyes, emulsifiers, buffers, cooling agents (eg, menthol). The excipients are present in conventional amounts ranging from about 0.001% to 5%—most commonly 0.001–2% but not to exceed a total of 10%.

The major ingredients of the gel vehicle should have a solubility parameter (see Vaugnn, supra) in the range of about 9–13.5, preferably 10–12; each of the major components will usually have a solubility parameter in the range of about 9–14, preferably about 9.5–12.5 (as an average of all of the components).

In some instances, one component may serve mere than one function. Salicylate compounds such as methyl salicylate or glycol salicylate may act both as solvents and as analgesics. There is therefore some flexibility in preparing the formulation, though it should provide a reasonable rate of penetration of the drug through the unit area of skin over a period of about 4–12 hours.

The local anesthetic compound may be present as an independent entity or as a salt of an analgesic or nonsteroidal anti-inflammatory drug. Salts of salicylic acid, acetylsalicylic acid (aspirin), indomethacin, and ketoprofen are suitable for topical transdermal delivery. Salts of anesthetic and analgesic may be prepared, eg lidocaine salicylate.

Analgesic drugs in concentrations of 1–10% are usually sufficient to reduce pain.

Other methods of application include aerosols, in which a gas is combined with the vehicle, and plasters. In the case of plasters, the covering is substantially impermeable to the compound and to other fluids.

For the plaster, the covering may be composed of polyvinyl chloride, Saran Wrap, polyethylene, synthetic rubber, woven or nonwoven polyethylene fabric, etc. The drug is dissolved in the adhesive with the aid of polypropylene glycol methyl salicylate, glycol salicylate, or other solvents.

The data on the following pages are offered by way of illustration and not by way of limitation.

EXPERIMENTAL MATERIALS AND METHODS

Patient Population

Claims for the effectiveness of the invention are supported by the results of a study undertaken by Rowbotham M. C. and Fields H. L., Department of Neurology, School of Medicine, University of California, San Francisco. This study entitled "Topical Lidocaine Reduces Pain in Post-Herpetic Neuralgia", presents data from experience with 11 patients who had well-established post-herpetic neuralgia (pain present for more than 3 months after healing of the rash of herpes zoster); well-demarcated areas of skin with marked allodynia (pain resulting from a nonnoxious stimulus to normal skin) from light stroking with a cotton wisp; and no medical contraindications to the use of local anesthetics.

Six women and five men participated in the study. The average was 70 years. Six patients had post-herpetic neuralgia that included the ophthalmic division of the trigeminal nerve, and five had post-herpetic neuralgia located in thoracic dermatomes.

The duration of pain ranged from 3 months to 12 years.

All subjects except two were in good general health. One patient had multiple cardiovascular problems, and another had widespread multiple myeloma.

In all cases, post-herpetic neuralgia was the only significant pain problem during the period of the study.

Formulation of Anesthetic Containing Compound

The local anesthetic preparation used in the study consisted of a 10% lidocaine in a gel vehicle. The vehicle consisted of 12% polysorbate-20, 0.9% carbomer 940, 0.8% diisopropanolamine, and 76.3% propylene glycol. Lidocaine gel was applied to the skin, and the area was covered with plastic food wrap (Saran Wrap) and the edges taped with 3M Micropore Adhesive Tape, taking care not to apply tape to hypersensitive skin.

In a further refinement for thoracic post-herpetic neuralgia, an adhesive plaster sheet (10×14 cm), with interwoven polyethylene fabric backing and 14 grams of adhesive containing 3.58% lidocaine and 2% methylsalicylate, was applied to affected areas of the backs of patients. The plaster formulation was found to he as effective as the occlusive dressing formulation in relieving pain associated with thoracic post-herpetic neuralgia.

Application of Compound

For thoracic post-herpetic neuralgia, the dosage of lidocaine applied as gel ranged from 240 to 500 mg.

Subjects with post-herpetic neuralgia involving trigeminal nerve were not treated in the same way. Instead, the gel provided was spread by the subject over areas of maximum pain and sensitivity on the forehead, temple, and scalp. The medication was not covered but was applied repeatedly to maintain contact. The dosage of lidocaine applied in this way ranged from 140 to 300 mg.

Pain Measurement

Pain was measured on the 100 mm pain VAS scale and a 100 mm pain relief VAS scale. The VAS (Visual Analog Scale) pain scale is defined by Littman G. S. et al in *Clin Pharmacol Ther* 1985;38:16–23. Pain levels were assessed every hour for 4 hours after lidocaine application. Blood pressures and pulse rates were recorded, and possible side effects were monitored. At 1 and 3 hours after lidocaine application, blood was drawn for determination of serum lidocaine levels.

Results

For the entire group of 11 subjects, pain VAS ratings declined steadily over the 4 hours of observation from a baseline mean of 35.5 mm±25.4 mm to a low of 14.2 mm±7.8 mm at 4 hours after application (P<0.01). Pain relief VAS ratings increased steadily during the observation period from 39.3 mm±39.9 mm at 1 hour after application to 59.6 mm±25.5 mm at 4 hours after application (P<0.01). Calculating the change in pain VAS scores from baseline for the observation period showed the largest decrease in pain score occurred at 3 hours after gel application. The decrease was 21.2 mm±19.4 mm (P=0.05).

There were significant differences in the manner in which patients with thoracic post-herpetic neuralgia and those with trigeminal post-herpetic neuralgia responded to the topical lidocaine. The five subjects with thoracic post-herpetic neuralgia had highly significant changes in pain ratings, especially during the last 2 hours of observation, from a baseline mean of 44.2 mm±21.6 mm to a low of 12.8 mm±8.7 mm (P<0.001). The results achieved with occlusive dressings and with the plaster formulation described below were equally good.

Subjects with trigeminal post-herpetic neuralgia also demonstrated a decline in pain VAS scores, but the observed changes were not statistically significant.

Analysis of pain relief also showed a difference in response between the two groups, but in both groups the mean peak pain relief ratings were greater than 50 mm. The greater pain relief experienced by the patients with thoracic post-herpetic neuralgia may be attributable to the enhancing effect of the occlusive covering and the transdermal penetration achieved with the plaster formulation.

Subjects reported no adverse effects of topical lidocaine during the period of the study. Changes in blood pressure and pulse were not significant. At both 1 and 3 hours after application, serologic tests revealed measurable blood levels of lidocaine in all subjects, but the concentration in all cases was below 1 microgram per milliliter.

All publications mentioned in this specification testify to the skills of those engaged in the art and science to which this invention pertains, and all are incorporated by reference herein just as if each individual publication was singled out for incorporation by reference.

The invention now having been fully described and the results of its use set forth, it will be apparent to one of ordinary skill in the art that many changes and modifications can be made thereto without departing from the spirit or scope of the appended claims.

What is claimed is:

1. A method for reducing pain associated with herpes-zoster and post-herpetic neuralgia, said method comprising:
   applying at the site of pain:
   (1) a composition comprising lidocaine in a physiologically acceptable vehicle capable of transdermal penetration for a time sufficient for said lidocaine to be transported across said skin to the site of pain involvement in an amount sufficient to relieve said pain, said vehicle comprising from 1–20 weight percent lidocaine, and;
   (2) an occlusive dressing of a physiologically acceptable plastic film;
   whereby extended pain relief is obtained substantially after said applying and after any anesthetic effect of such lidocaine is terminated.

2. A method according to claim 1, wherein said occlusive dressing Saran Wrap, polyethylene film, or polyvinyl and is impermeable to the composition.

3. A method according to claim 1, wherein said dressing is a plaster dressing wherein said lidocaine is incorporated into the adhesive layer of said plaster.

4. A method for reducing pain associated with herpes-zoster and post-herpetic neuralgia for extended periods of time, said method comprising:
   a. applying to the skin at the site of pain a composition comprising lidocaine in a concentration of about 5–15% in a physiologically acceptable vehicle capable of transdermal penetration for a time sufficient for said lidocaine to be transported across said skin to the site of involvement in an amount sufficient to relieve pain, said vehicle comprising: a glycol in about 75–85%; a nonionic surfactant in about 2–20%; and a thickening agent in about 0.1–5%; and
   b. covering the composition with a plastic film as an occlusive dressing or as a plaster dressing simultaneously or consecutively with said applying;
   whereby extended pain relief is obtained substantially after said applying and after any anesthetic effect of said lidocaine is terminated.

5. A method for reducing pain associated with herpes-zoster and post herpetic neuralgia for extended periods of time, said method comprising:
   applying to the skin at the site of pain a plaster which comprises a composition which comprises lidocaine as the base form in a concentration of about 1–20 weight % incorporated into the adhesive layer of said plaster.

6. A method for reducing pain associated with herpes-zoster and post-herpetic neuralgia, said method comprising:
   applying at the site of pain:
   (1) a composition comprising lidocaine in a physiologically acceptable vehicle capable of transdermal penetration for a time sufficient for said lidocaine to be transported across said skin to the site of pain involvement in an amount sufficient to relieve said pain, said vehicle comprising from 1–20 weight percent lidocaine, and;
   (2) a plaster dressing wherein said anesthetic is incorporated into the adhesive layer of said plaster;
   whereby extended pain relief is obtained substantially after said applying and after any anesthetic effect of such lidocaine is terminated.

* * * * *